(12) United States Patent
Rhrissorrakrai et al.

(10) Patent No.: US 11,211,148 B2
(45) Date of Patent: Dec. 28, 2021

(54) TIME-SERIES PHYLOGENETIC TUMOR EVOLUTION TREES

(71) Applicant: International Business Machines Corporation, Armonk, NY (US)

(72) Inventors: Kahn Rhrissorrakrai, Woodside, NY (US); Filippo Utro, Pleasantville, NY (US); Chaya Levovitz, New York, NY (US); Laxmi Parida, Mohegan Lake, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 779 days.

(21) Appl. No.: 16/022,075

(22) Filed: Jun. 28, 2018

(65) Prior Publication Data

US 2020/0004927 A1    Jan. 2, 2020

(51) Int. Cl.
*G16B 45/00* (2019.01)
*G16H 20/40* (2018.01)
*G16H 50/20* (2018.01)

(52) U.S. Cl.
CPC ............. *G16B 45/00* (2019.02); *G16H 20/40* (2018.01); *G16H 50/20* (2018.01)

(58) Field of Classification Search
CPC ......... G16H 20/40; G16H 50/20; G16H 50/50
See application file for complete search history.

(56) References Cited

U.S. PATENT DOCUMENTS

| 7,917,306 | B2 | 3/2011 | Frumkin |
| 9,340,774 | B2 | 5/2016 | Damelin |
| 9,569,586 | B2 | 2/2017 | Rubben |
| 2002/0198664 | A1 | 12/2002 | Shackney |

(Continued)

FOREIGN PATENT DOCUMENTS

| WO | 2014152990 A1 | 9/2014 |
| WO | 2017197351 A1 | 11/2017 |

OTHER PUBLICATIONS

Bozic et al., "Quantifying Clonal and Subclonal Passenger Mutations in Cancer Evolution." PLOS Computational Biology, DOI:10.1371/journal.pcbi.1004731 Feb. 1, 2016, 1-19.

(Continued)

*Primary Examiner* — Peter R Egloff
(74) *Attorney, Agent, or Firm* — Cantor Colburn LLP; Kristofer Haggerty

(57) ABSTRACT

A computer-implemented method incudes calculating, by a processor, based on sequence data for a tumor from a subject at a plurality of time points, a mutation frequency for each of a plurality of SSVs at each of the time points to provide a plurality of time-resolved mutation frequencies (between 0 and 1) for each of the plurality of SSVs, the sequence data including a plurality of simple somatic variations (SSVs) at each of the time points; binning, by the processor, the plurality of time-resolved mutation frequencies for each SSV at each of the time points to provide a matrix of SSVs and time points; converting, by the processor, the matrix cells to pseudo-clones; and constructing, by the processor, a time-series tumor evolution tree from the pseudo-clones, wherein each time point in the time-series evolution tree represents an event in the subject's cancer treatment.

9 Claims, 11 Drawing Sheets

(56) References Cited

U.S. PATENT DOCUMENTS

| | | | |
|---|---|---|---|
| 2005/0038609 | A1 | 2/2005 | Benner |
| 2009/0186024 | A1 | 7/2009 | Nevins |
| 2009/0292482 | A1 | 11/2009 | Frumkin |
| 2012/0158391 | A1 | 6/2012 | Vaske et al. |
| 2013/0011393 | A1 | 1/2013 | Lancaster |
| 2013/0332083 | A1 | 12/2013 | Van Laar et al. |
| 2015/0261912 | A1 | 9/2015 | Sanborn |
| 2016/0357902 | A1 | 12/2016 | Yasuda |
| 2017/0298441 | A1 | 10/2017 | Wu |
| 2017/0321281 | A1 | 11/2017 | Iavarone |
| 2018/0001184 | A1 | 1/2018 | Tran |
| 2018/0080090 | A1 | 3/2018 | Faham |
| 2018/0100201 | A1 | 4/2018 | Garraway |
| 2019/0106751 | A1* | 4/2019 | Zimmermann ...... C12Q 1/6858 |
| 2019/0249261 | A1* | 8/2019 | Dingli .................... G16H 50/20 |

OTHER PUBLICATIONS

El-Kebir et al., "Reconstruction of clonal trees and tumor composition from multi-sample sequencing data." Bioinformatics, 31, 2015, i62-i70.

Jiang et al., "Assessing Intratumor Heterogeneity and Tracking Longitudinal and Spatial Clonal Evolutionary History by Next-Generation Sequencing." Proceedings of the National Academy of Sciences of the United States of America 113.37 (2016): E5528-E5537. PMC. Web. May 15, 2018.

Malikic et al., "Clonality inference in multiple tumor samples using phylogeny." Bioinformatics, vol. 31, Issue 9, May 1, 2015, pp. 1349-1356.

Manica et al., "Inferring clonal composition from multiple tumor biopsies," ARXIV, https://arxiv.org/abs/1701.07940. Jan. 2017.

Xia, L. et al.; "SVEngine: an efficient and versatile simulator of genome structural variations with features of cancer clonal evolution"; GigaScience, vol. 7, Issue No. 7; 2018; 12 pages.

Liang et al., "An Improved Binary Differential Evolution Algorithm to Infer Tumor Phylogenetic Trees", Biomed Research International, doi.org/10.1155/2017/5482750, 2017.

Roth et al., "PyClone: Statistical inference of clonal population structure in cancer", Nat Methods. Apr. 2014; 11(4): 396-398. doi:10.1038/nmeth.2883.

Deshwar et al., "PhyloWGS: Reconstructing subclonal composition and evolution from whole-genome sequencing of tumors", Genome Biology, doi:10.1186/s13059-015-0602-8, 2015.

Satas et al., "Tumor phylogeny inference using tree-constiained importance sampling", Bioinformatics, 33, pp. i152-i160, doi: 10.1093/bioinformatics/btx270, 2017.

Dang et al., "ClonEvol: clonal ordering and visualization in cancer sequencing", Annals of Oncology, 28, pp. 3076-3082, doi:10.1093/annonc/mdx517, 2017.

List of IBM Patents or Patent Applications Treated as Related; Date Filed: Sep. 4, 2018, 2 pages.

Utro et al., "Functional Analysis of Time-Series Phylogenetic Tumor Evolution Tree," U.S. Appl. No. 16/022,088, filed Jun. 28, 2018.

Utro et al., "Phylogenetic Tumor Evolution Trees With Distribution of Variants in Cell Populations," U.S. Appl. No. 16/120,630, filed Sep. 4, 2018.

* cited by examiner

Assumption 1 — 801

Let n pseudo-clones be identified by SNP sets $A_i$, $1 \leq i \leq n$, then:

For any pair $1 \leq i_1 \neq i_2 \leq n$, the following holds: $A_{i_1} \cap A_{i_2} = \emptyset$.

For each i and for any pair, $r_1, r_2 \in A_i$, the following holds: $f(r_1) \approx f(r_2)$

Lemma 1.1 — 802

Let r be an SNP observed in the tumor and A be a pseudo-clone.
1. Then r belongs to exactly one pseudo-clone.
2. Then $f(A)$, CCF of A, is well defined with $f(A) = f(x \in A)$

Lemma 1.2 — 803

If in a tumor sample, $f(A_1) + f(A_2) > 1$, then $A_1$ and $A_2$ must be pseudo-clones.

TIME-SERIES PHYLOGENETIC TUMOR EVOLUTION TREES

BACKGROUND

The present invention generally relates to computing systems, and more specifically, to time-series tumor evolution trees.

Tumors include a plurality of distinct cell populations. Massively parallel sequencing allows for the detection of somatic variants that correspond to cellular subpopulations in a tumor. Collections of somatic variants, such as single nucleotide polymorphisms (SNPs) or other variants, are referred to as clones. Phylogenetic clone trees thus represent evolutionary relationships among genetic cell lineages in the tumor.

SUMMARY

Embodiments of the present invention are directed to a computer-implemented method for determining a time-series tumor evolution tree. A non-limiting example of the computer-implemented method incudes calculating, by a processor, based on sequence data for a tumor from a subject at a plurality of time points, a mutation frequency for each of a plurality of SSVs at each of the time points to provide a plurality of time-resolved mutation frequencies for each of the plurality of SSVs, wherein the mutation frequency is between 0 and 1, wherein the sequence data includes the plurality of simple somatic variations (SSVs) at each of the time points, wherein N is the number of SSVs and K is the number of time points; binning, by the processor, the plurality of time-resolved mutation frequencies for each SSV at each of the time points to provide an N×K matrix; removing matrix rows, by the processor, wherein the time-resolved mutation frequencies are less than a threshold value, and merging similar rows, to provide an N'×K matrix, wherein N'≤N; converting, by the processor, the N'×K matrix cells to pseudo-clones, wherein each pseudo-clone represents a collection of matrix cells defined by a set of SSVs having a defined time-resolved mutation frequency, wherein each SSV is assumed to belong to exactly one pseudo-clone, and wherein it is assumed that each SSV cannot return to its unmutated state; and constructing, by the processor, a time-series tumor evolution tree from the pseudo-clones, wherein each time point in the time-series evolution tree represents an event in the subject's cancer treatment.

Embodiments of the invention are directed to a computer program product for determining a time-series tumor evolution tree, the computer program product comprising a computer readable storage medium having program instructions embodied therewith. The program instructions are executable by a processor to cause the processor to perform a method. A non-limiting example of the method includes calculating, by the processor, based on sequence data for a tumor from a subject at a plurality of time points, a mutation frequency for each of a plurality of SSVs at each of the time points to provide a plurality of time-resolved mutation frequencies for each of the plurality of SSVs, wherein the mutation frequency is between 0 and 1, wherein the sequence data includes the plurality of simple somatic variations (SSVs) at each of the time points, wherein N is the number of SSVs and K is the number of time points; binning, by the processor, the plurality of time-resolved mutation frequencies for each SSV at each of the time points to provide an N×K matrix; removing matrix rows, by the processor, wherein the time-resolved mutation frequencies are less than a threshold value, and merging similar rows, to provide an N'×K matrix, wherein N'≤N; converting, by the processor, the N'×K matrix cells to pseudo-clones, wherein each pseudo-clone represents a collection of matrix cells defined by a set of SSVs having a defined time-resolved mutation frequency, wherein each SSV is assumed to belong to exactly one pseudo-clone, and wherein it is assumed that each SSV cannot return to its unmutated state; and constructing, by the processor, a time-series tumor evolution tree from the pseudo-clones, wherein each time point in the time-series evolution tree represents an event in the subject's cancer treatment.

Embodiments of the present invention are directed to a system for determining a time-series evolution tree. A non-limiting example of the system includes a processor; and a computer readable storage medium storing executable instructions that, when executed by the processor, cause the processor to perform operations including: calculating, by a processor, based on sequence data for a tumor from a subject at a plurality of time points, a mutation frequency for each of a plurality of SSVs at each of the time points to provide a plurality of time-resolved mutation frequencies for each of the plurality of SSVs, wherein the mutation frequency is between 0 and 1, wherein the sequence data includes the plurality of simple somatic variations (SSVs) at each of the time points, wherein N is the number of SSVs and K is the number of time points; binning, by the processor, the plurality of time-resolved mutation frequencies for each SSV at each of the time points to provide an N×K matrix; removing matrix rows, by the processor, wherein the time-resolved mutation frequencies are less than a threshold value, and merging similar rows, to provide an N'×K matrix, wherein N'≤N; converting, by the processor, the N'×K matrix cells to pseudo-clones, wherein each pseudo-clone represents a collection of matrix cells defined by a set of SSVs having a defined time-resolved mutation frequency; and constructing, by the processor, a time-series tumor evolution tree from the pseudo-clones, wherein each time point in the time-series evolution tree represents an event in the subject's cancer treatment.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 8 is a flowchart of assumption 1 and lemmas 1.1 and 1.2 of the model according to the invention;

Figure 1:
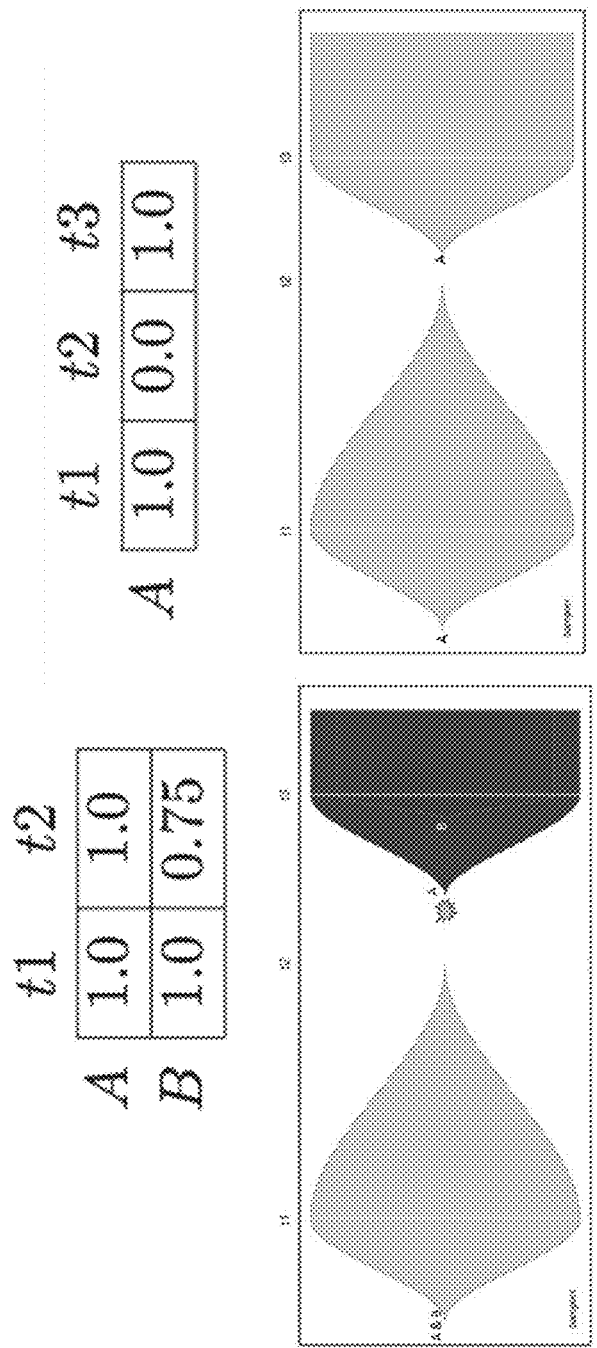
FIG. 1 depicts a pair of Fishplots showing discontinuities in tumor evolution according to embodiments of the invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" can be understood to include any integer number greater than or equal to one, i.e. one, two, three, four, etc. The terms "a plurality" can be understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Turning now to an overview of technologies that are more specifically relevant to aspects of the invention, phylogenetic clone trees have been constructed to represent evolutionary relationships among genetic cell lineages in a tumor. Typically, multiple samples from a patient's tumor are obtained, combined, and massively paralleled sequenced. Clustering of variants is used to infer the clonal evolution of the tumor. Various methods have been developed for the construction of phylogenetic clone trees such as PyClone, PhyloWGS, ClonEvol, and others.

Several definitions are provided. A variant is defined as a change in the most common genetic sequence. Variants can include single nucleotide variants (SNVs), which are single nucleotide variations, and indels, which are insertions/deletions, typically of 1 to 50 bases. SNVs and indels are collectively referred to as simple somatic variations (SSVs). The cancer cell fraction (CCF) of a variant is the fraction of sample with a particular variant. The variant allele frequency (VAF) is the relative frequency of a variant in a population, expressed as a fraction or percentage. The copy number variation (CNV) is when the number of copies of a particular gene varies.

As used herein, a clone is a collection of cells that are indistinguishable with respect to their SSVs. In other words, all the cells of a clone have the same set of SSVs. A pseudo-clone is a collection of cells defined by a set of SSVs, but that can have additional variants in addition to the set. For example, a pseudo-clone is defined by the set of SSVs called A, but can have additional SSVs in addition to those included in A. The term "pseudo" refers to the identifying signature A that defines the clone, since the actual distinguishing SSVs for the clone could be a non-trivial superset of A.

An aspect that is missing from current phylogenetic evolution trees is the phase change, that is, when the mutation defining the variant occurs during the time course of the tumor evolution, such as when a treatment is administered to the subject. Such phase changes are not obvious from the time series values of frequencies (e.g., VAF/CCF) of variants. Construction of tumor phylogenetic trees that can simultaneously represent the explicit time points the samples were taken, the dynamic frequencies of the clones, and the compositional changes of clonal populations to allow the identification of the clones that grow and shrink, for example, in response to patient treatment. This identification of clones can, for example, enable a user to determine the timing for the next assay time given projected or similar trees. In addition, the detection of the responder/non-responder status, that is, the resistant/sensitive status of the tumor, with respect to treatment can be determined.

Turning now to an overview of the aspects of the invention, one or more embodiments of the invention address the above-described shortcomings of the prior art by providing a time-dependent method for constructing phylogenetic clone trees that includes tracking the frequencies of pseudo-clones.

The above-described aspects of the invention address the shortcomings of the prior art by enabling the identification of pseudo-clones that grow and shrink over time, such as in response to patient treatment. The time-series tumor evolution trees of the invention can represent the phase shift of clones that can appear or disappear over time. Unlike most phylogenetic trees, time-series trees can be used to explicitly compare the cancer evolution to the sampled time points and the patient's treatment history. Such identification will enable the user to determine the timing for the next assay time given projected or similar trees and/or to detect the responder/non-responder status or the resistant/sensitive status of the tumor with respect to treatment.

Figure 6:
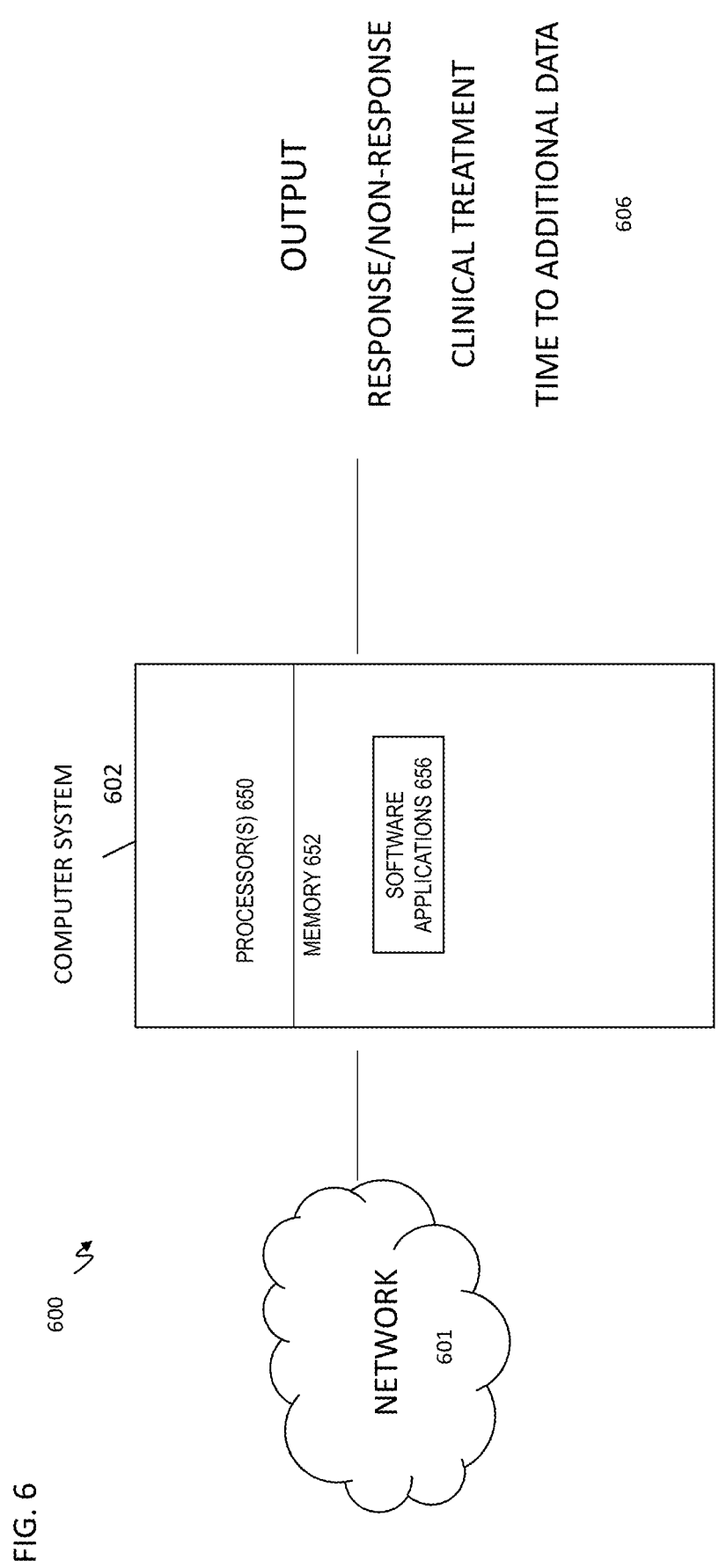
FIG. 6 illustrates a system for constructing a time-series tumor evolution tree according to embodiments of the present invention.

Turning now to a more detailed description of aspects of the present invention, described is an implementation of the method, e.g., by computer system 602 depicted in FIG. 6. If r is an SSV in a tumor sample, then the CCF value of r can be written as $0 \leq f(r) \leq 1$. The frequency can be expressed as either VAF or CCF, calculated at each timepoint. SSVs are then binned, e.g., by processor 605 and software applications 656 depicted in FIG. 6, in accordance with their frequency. An exemplary method of binning is Jenk's Natural Breaks. Thus, the input of the method, e.g., a computer-implemented method, is a plurality of SSVs and their frequencies at each time point in the time-series, for example, at least at a first time point and a second time point. For example, if the Jenk's Natural Breaks method is used, for each time point, a set of non-overlapping intervals of the range [0,1] is determined (e.g., [0, 0.2[, [0.2, 0.5[, [0.5,1.0]) for each set the number of SSV with f(r) value is counted.

Figure 7:
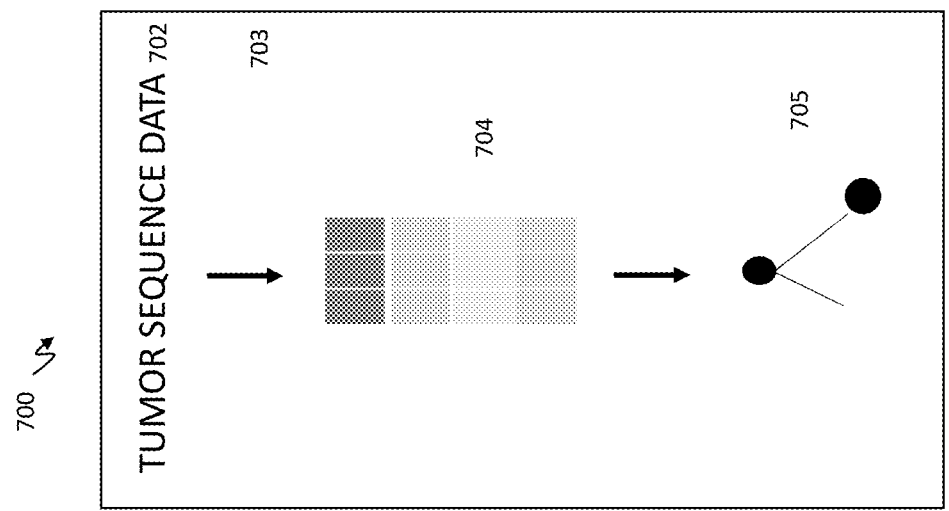
FIG. 7 illustrates a computer-implemented method for constructing a time-series tumor evolution tree according to embodiments of the present invention.

More specifically, aspects of the computer-implemented method 700 executed by the software application 656 are illustrated in FIG. 7. Tumor sequence data 702 is obtained including a plurality of SSVs and their frequencies at a plurality of time-points in a subject's cancer treatment. The SSVs are binned according to their frequencies, e.g., by processor 605 and software applications 656 depicted in FIG. 6, to provide a matrix 704 of SSVs and their frequencies at each of the plurality of time-points. The matrix 704 is then used to construct a time-series phylogenetic tree 705 e.g., by processor 605 and software applications 656 depicted in FIG. 6, for the subject.

Figure 9:
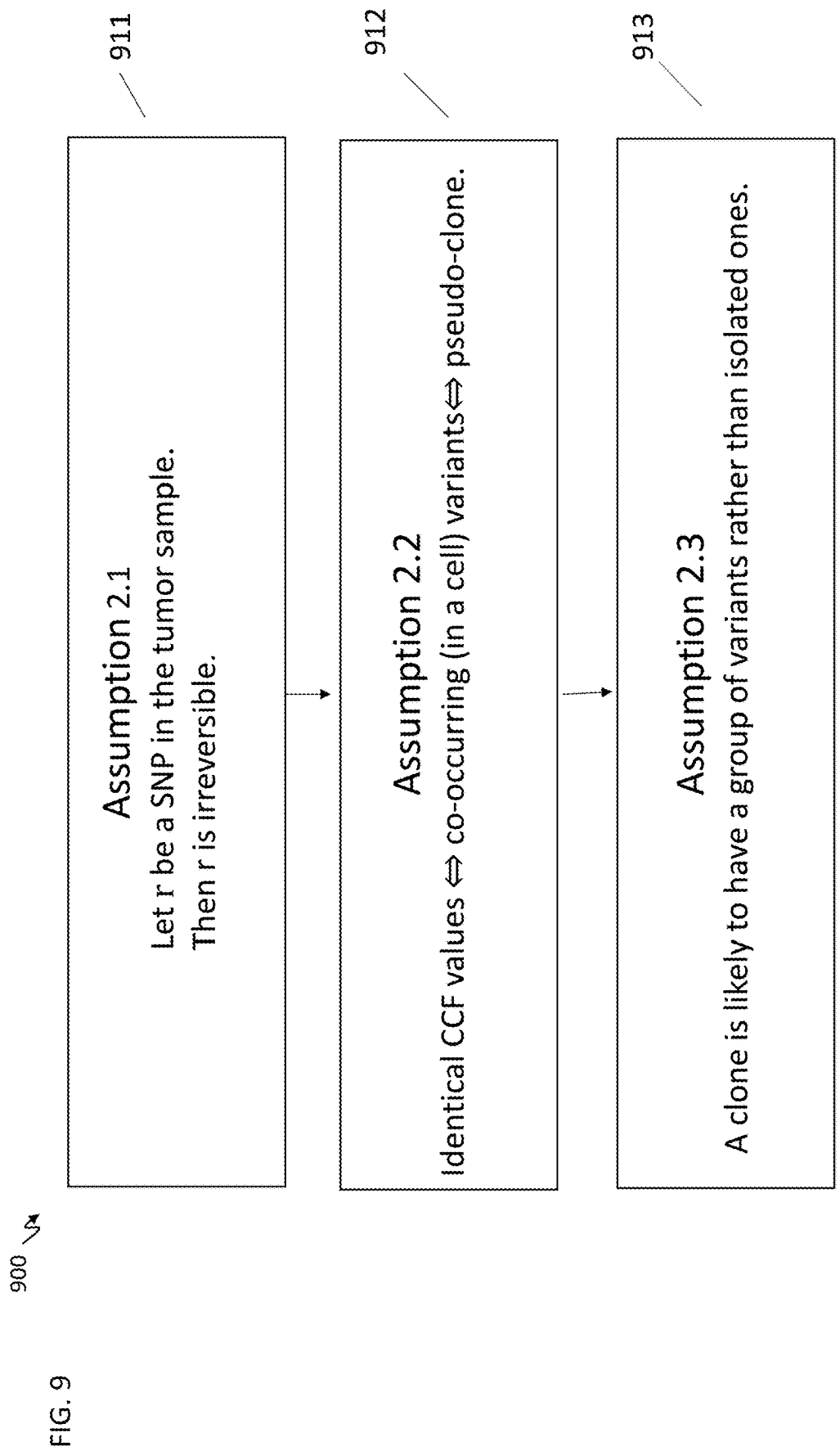
FIG. 9 is a flowchart of assumptions 2.1, 2.2 and 2.3 of the model of the invention.

The model optionally includes several assumptions as detailed below. The processor 650 executes the software application 656 (depicted in FIG. 6) which includes the model and optional assumptions. FIGS. 8 and 9 provide flowcharts 800 and 900 of the assumptions 1 and 2 that can be included in the model in the software application 656 for execution by the processor 650.

Assumption 1, 801 in FIG. 8. Let n pseudo-clones be identified by SNP sets $A_i$, $1 \leq i \leq n$, then:
1. For any pair $1 \leq i_1 \neq i_2 \leq n$, the following holds: $A_{i_1} \cap A_{i_2} = \emptyset$.
2. For each i and for any pair, $r_1, r_2 \in A_i$, the following holds: $f(r_1) \approx f(r_2)$ Lemma 1.1, 802 in FIG. 8. Let r be an SNP observed in the tumor and A be a pseudo-clone.
1. Then r belongs to exactly one pseudo-clone.
2. Then f(A), CCF of A, is well defined with $f(A) = f(x \in A)$ Lemma 1.1 follows directly from Assumption 1. Note that this does not hold for a non-pseudo-clone. This characteristic of the pseudo-clone provides a convenient handle to the computational methods.

The mathematical manipulation of CCF values obtained from bulk or multi-cell sequencing, e.g., by the software application 656 (depicted in FIG. 6), provides information to reconstruct pseudo-clones. Since the information about the multi-way overlap of SNPs is missing, identical CCF values are used as a proxy for co-occurrence. While one can construct counter-examples for this, this is only an assumption.

Lemma 1.2, 803 in FIG. 8. If in a tumor sample, $f(A_1) + f(A_2) > 1$, then $A_1$ and $A_2$ must be pseudo-clones.

This helps address the question, when one is dealing with a tumor sample with clones and their CCF values, whether they are indeed clones or a mathematically convenient pseudo-clones. For instance, if $f(A_1) = 1.0$ and there exists at least another $0 < f(A_2) < 1.0$, then $A_1$ and $A_2$ must be pseudo-clones.

Assumptions 2.1-2.3 are shown, in FIG. 9. Let r be a SNP in the tumor sample.

Assumption 2.1, 911 in FIG. 9. Then r is irreversible, i.e., once the mutation occurs the reverse mutation of turning it back to its original state does not occur. The rationale for this assumption is that if it appears like a back mutation has occurred, then is it due to metastasis of cells from a different location or due to error in the CCF. This scenario can be disallowed for cleanliness of the model, so that the model is not overrun with exceptions.

This assumption, however, can bring about a discontinuity in the tumor evolution (see FIG. 1). As shown in FIG. 1, at time t1, all mutations A and B belong to the same group (i.e., they are indistinguishable), the clones "die" at time t2, and at time t3, mutations A and B break into two separate groups. The standard Fishplot representation of FIG. 1 does not allow this configuration, which is pointed out with the asterisk in the plot. That is, the asterisk birth point indicates that these progenitor cells come from elsewhere and cannot have originated from the evolving tumor. Thus, the Fishplot representation has insufficient granularity to represent these likely progenitor events.

Assumption 2.2, 912 in FIG. 9. Identical CCF values ⇔ co-occurring (in a cell) variants ⇔ pseudo-clone.
Approximation: In practice similar, but perhaps not identical, CCF values define a clone
Rationale: The variance is due to numerical or other inaccuracies in the CCF computation Assumption 2.3, 913 in FIG. 9. A clone is likely to have a group of variants rather than isolated ones.

For example, Let A, B, C, D, . . . be non-overlapping sets of SNPs identifying the respective pseudo-clones. For convenience, $f(A) = a$, $f(B) = b$, $f(C) = c$, and so on. Now that we can distinguish the mathematical difference between clones and pseudo-clones, in the rest of the discussion we sacrifice conciseness for simplicity of exposition and refer to the pseudo-clones as clones. While the grouping if SSVs can be adjusted for a specific sample/patient/disease context, the frequency of SSVs grouped into a pseudo-clone can, for example, differ by less than 10%, preferably less than 5%.

Figure 2:
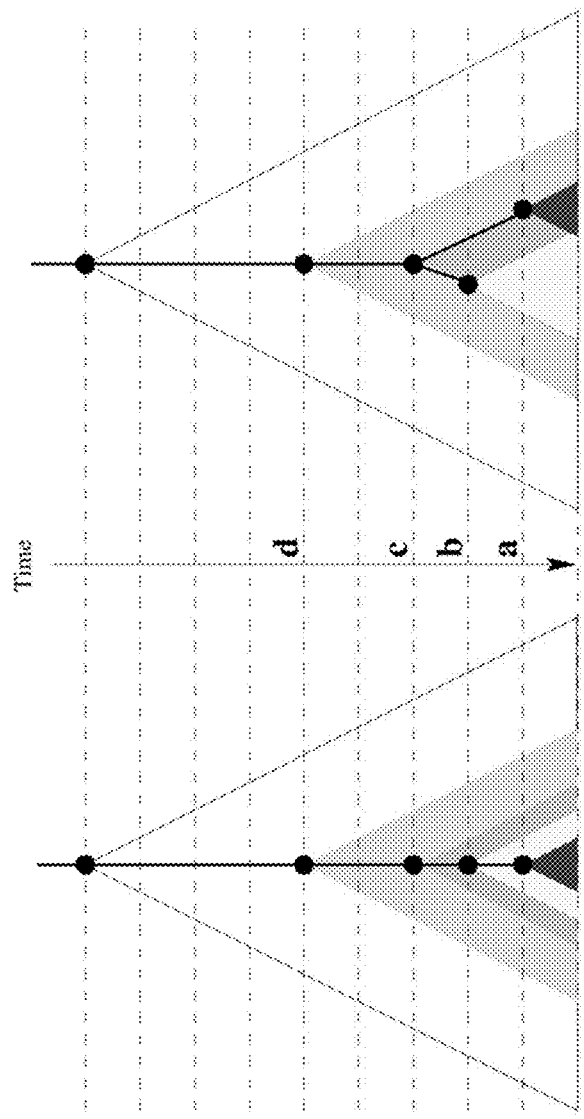
FIG. 2 depicts two possible ways a series of non-overlapping SNPS stack up according to embodiments of the invention.

The question of how multiple sets of SSVs stack up against each other is left up to the computational method, which is incorporated in the software application 656 executed by the processor 650. For example, two possible ways the mutations can stack up as shown in FIG. 2. Let A, B, C, D be non-overlapping sets of SNPs such that d>c>b>a>0. The time axis is the molecular clock. The difference between the left and the right structure is that while the one on the left suggests that there exist cells that have both A (black) and B (white) mutations the one on the right suggests that there are no cells that have both these sets of mutations. Currently, these two scenarios cannot be teased apart. For simplicity, the scenario that is the most parsimonious is selected, which in this case is the left one.

Using the foregoing assumptions in the model, an embodiment of a birth-death tumor evolution tree time series is described. A processor 650 executes a software application 656 (depicted in FIG. 6) to create the time-series tumor evolution tree 400 in FIG. 4, for example. Input: Let M be a N×K matrix where N is the number of SSVs and K is the number of time points. Each time point in the evolution tree represents an event in the subject's cancer treatment 0≤M[i,k]≤1 is the CCF (or VAF) value of SNP i at time point k.

Method, performed by processor 650 executing software application 656:

1. Preprocess M based on Assumption 2.1, such that the following holds.

$$(M[i,t_{k_1}]=1) \Rightarrow (M[i,t_{k_2}]=1), \forall\ t_{k_2} \geq t_{k_1}.$$

This means that if a mutation is present at a given time point 1, it will also be present at subsequent time point 2.

2. Based on Assumption 2.2, bin the SSVs at each time point. At time point $t_k$ let the bins be $C_1^k, C_2^k, \ldots, C_{n_k}^k$, where $1 \leq t_k < K$ and $n_k$ is the number of bins at time point $t_k$. Let the CCF values be $c_1^k, c_2^k, \ldots, c_{n_k}^k$ respectively.

In some embodiments, use the Jenk's binning method as follows:
  a. Further preprocess each column to have no-repeating unique values.
  Rationale: Without this preprocessing, the light bins (the ones with fewer elements) become unduly large intervals. For example, an interval such as [0.20, 0.66]. The intervals are more important than the number of SSVs that support them.
  b. Do not fix the number of bins but use the Goodness of Variance Fit (GVF) value to determine the number of bins for an acceptable 0≤GVF≤1 value. For example, use a range of [0.75,0.82] values to get different possible bins or pseudo-clone definitions. That is, the model does not assume that the number of pseudo-clones, so the GVF allows assessment, on a sample by sample basis, of how many clones there are. For example, if the range of values observed for a sample was [0.7,0.9], there can be a different number of bins than if the range were [0,0.9]

The binning produces M' an N×K matrix as follows:
  $M'[i,t_k]=1$ if $M[i,t_k] \in C_l^k$, where $1 \leq l \leq n_k$.

In words, each mutation is assigned to a specific pseudo-clone.

3. Based on Assumption 2.3, remove the rows of M' where the row pattern is less than a threshold number. Also, merge similar patterns to account for possible numerical inaccuracies in the input.

Let this truncated matrix be M" be N'×K where N'≤N.

4. Convert the N'×K matrix cells to pseudo-clones. Each pseudo-clone represents a collection of cells defined by a set of SSVs having a defined time-resolved mutation frequency.

5. Construct the time-series tumor evolution tree based on the identified pseudo-clones, wherein each time point in the evolution tree represents an event in the subject's cancer treatment.

In an example, the pseudo-clone identification occurs in first time-point via the binning and GVF. Pseudo-clones at this first time-point are placed in the evolution tree in the most parsimonious manner, i.e. least disjoint, according to their frequency, with the most frequent closer to the root. With each subsequent time-point, the binning of the previous clones is used to determine if a branching has occurred. Additionally, if new pseudo-clones appear (e.g., those mutations now with a non-zero frequency value where in the first time-point they were zero), they are represented as a new pseudo-clone population emerging from the root pseudo-clone, or if they bin within an existing pseudo-clone, they will be added as an expansion of the pseudo-clone. Similarly, if there are pseudo-clones whose frequency moves to zero, then that is viewed as a death and the pseudo-clone is terminated in the tree.

Disjoint friendly Principle. The structure on the left in FIG. 2 is the least "disjoint-friendly". In other words if there is a mathematical possibility of the two sets being disjoint, the most "disjoint-friendly" option is selected. In other words, if there is a mathematical possibility of the two sets of being siblings, then the structure reflects that. In other words, when comparing two potentially equivalent trees, if there is a real mathematical possibility the branching into siblings is valid, then branching into siblings is selected.

When the mathematical possibility allows for both disjoint or overlap, then we use the Disjoint-friendly Principle to make the choice.

Foreign Progenitor: If a progenitor cell must come from the outside and not from the putative progenitor of the cells at the very first time point, then it is a foreign progenitor. For example, foreign progenitors can arise in metastasis. For example, if the sample data does not fit into the tree model as described, then it is likely that there is a foreign progenitor cell involved, perhaps from a metastatic event, and such foreign progenitor cells must be treated differently. The inventive method can thus help to identify cases where there is a foreign progenitor in the tumor sample.

EXAMPLE 1

Figure 3:
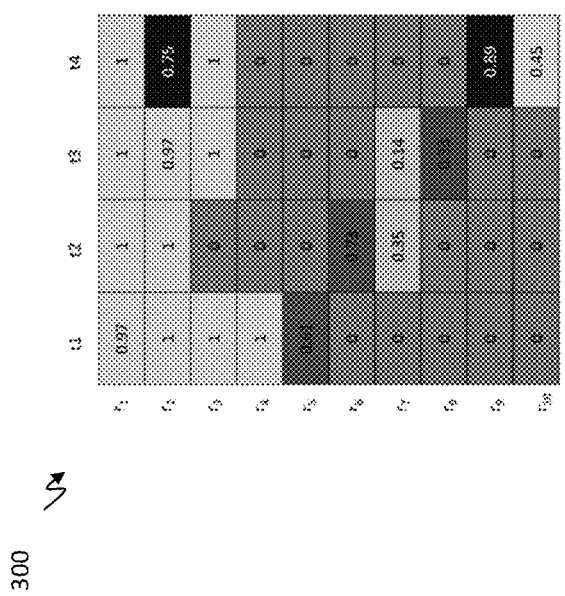
FIG. 3 depicts a binned mutation frequency table with SSVs as rows and time points as columns.
Figure 4:
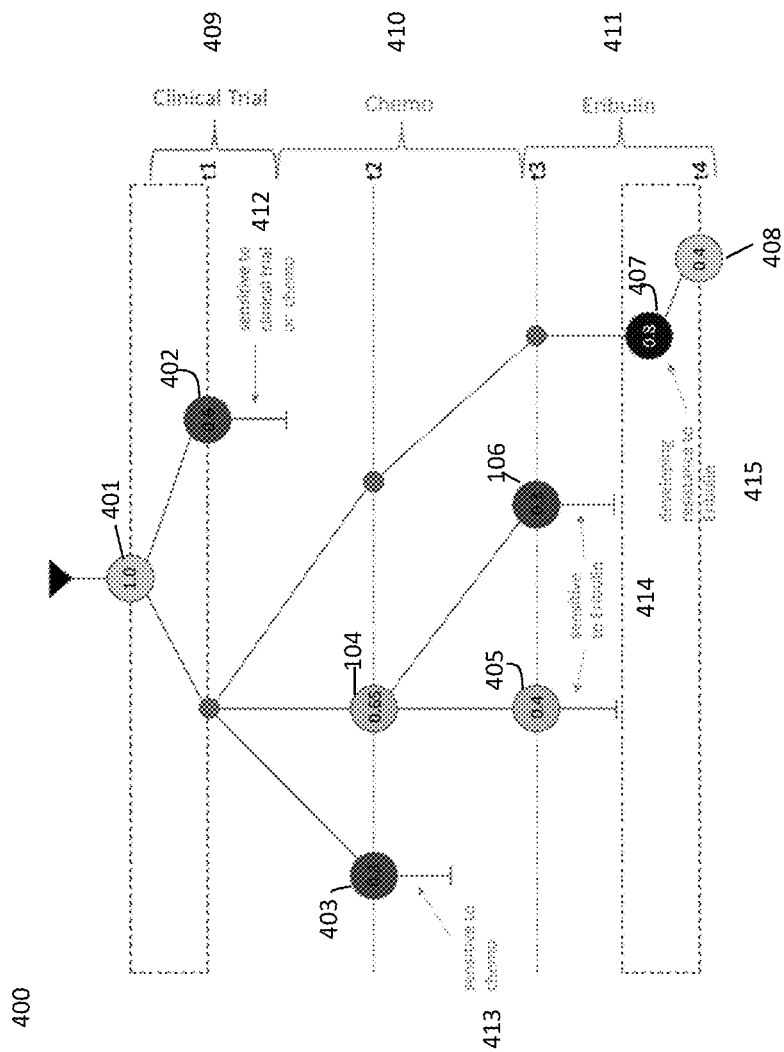
FIG. 4 depicts a tumor evolution tree with treatment information and likely points of resistance and sensitivity to treatments according to embodiments of the invention.
Figure 5:
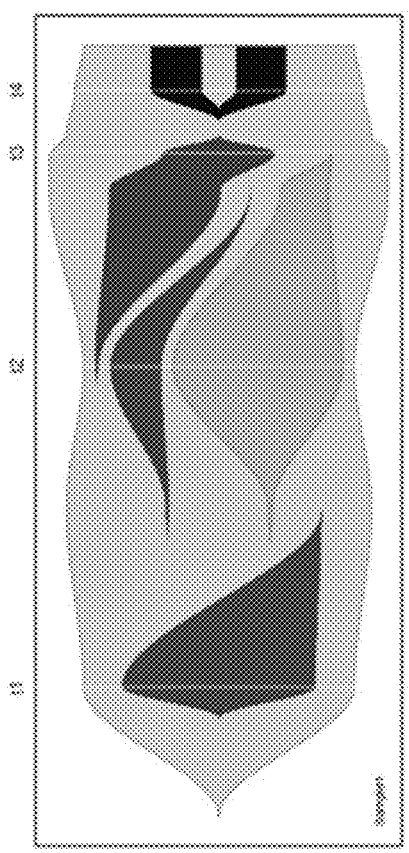
FIG. 5 depicts a Fishplot plot representation of the tumor evolution according to embodiments of the invention.

Consider a patient with four time points, that is, K=4. FIG. 3 shows an exemplary matrix 300 for the binned SSVs for each time point and the shading indicates the mutation patterns that can be represented as BIRTH-DEATH TUMOR EVOLUTION TREE 400 in FIG. 4. The representation in FIG. 4 has been annotated with the treatment information of the patient, highlighting possible resistance/responsive mechanisms in its tumor evolution. Specifically, FIG. 4 illustrates a time-series tumor evolution tree 400 with time point-specific clones 401-408, and with treatments 409-411 and treatment responses 412-415 indicated. The frequency the clone appears in the tumor at a given time point is shown by the value within the node. A processor 650 executes a software application 656 (depicted in FIG. 6) to create the time-series tumor evolution tree 400 in FIG. 1. This information can induce possible new treatment action for the patient itself or other patients with similar mutation patterns. A Fishplot is shown in FIG. 5 as a complementary representation of the data in FIG. 3.

In an aspect, the subject's cancer treatment includes radiation therapy, surgery, chemotherapy, targeted therapy, hormone therapy, immunotherapy, stem cell transplant, or a combination including at least one of the foregoing.

In an aspect, determining by the processor, a further treatment for the subject, includes comparing the time-series evolution tree composition with a database determined from a plurality of tumors from a plurality of subjects.

In another aspect, the further treatment includes a signal transduction pathway inhibitor, an antimetabolite, an anti-microtubule agent, an alkylating agent, a nitrogen mustard, a nitrosourea, a platinum agent, an anthracycline, an anti-biotic, a topoisomerase inhibitor, an alkyl sulfonate, a tri-azine, an ethyenimine, a folic acid analog, a pyrimidine analogue, a purine analog, an antitumor antibiotic, a hormone, an anti-angiogenic agent, an immunotherapeutic agent, a cell cycle signaling inhibitor, or a combination including one or more of the foregoing.

More specifically, further treatment thus include signal transduction pathway inhibitors (e.g., ErbB inhibitors, EGFR inhibitors such as erlotinib), antimetabolites (e.g., 5-fluoro-uracil, methotrexate, fludarabine), antimicrotubule agents (e.g., vincristine, vinblastine, taxanes such as paclitaxel, docetaxel), an alkylating agent (e.g., cyclophosphamide, melphalan, biochoroethylnitrosurea, hydroxyurea), nitrogen mustards, (e.g., mechloethamine, melphan, chlorambucil, cyclophosphamide and Ifosfamide); nitrosoureas (e.g., carmustine, lomustine, semustine and streptozocin;), platinum agents (e.g., cisplatin, carboplatin, oxaliplatin, JM-216, C 1-973), anthracyclines (e.g., doxrubicin, daunorubicin), antibiotics (e.g., mitomycin, idarubicin, adriamycin, daunomycin), topoisomerase inhibitors (e.g., etoposide, camptothecins), alkyl sulfonates including busulfan; triazines (e.g., dacarbazine); ethyenimines (e.g., thiotepa and hexamethylmelamine); folic acid analogs (e.g., methotrexate); pyrimidine analogues (e.g., 5 fluorouracil, cytosine arabinoside); purine analogs (e.g., 6-mercaptopurine, 6-thioguanine); antitumor antibiotics (e.g., actinomycin D; bleomycin, mitomycin C and methramycin); hormones and hormone antagonists (e.g., tamoxifen, cortiosteroids), anti-angiogenic agents (bevacizumab, endostatin and angiostatin), immunotherapeutic agents (transfection with cytokines such as interleukin 2, interleukin 4 or granulocyte-macrophage colony stimulating factor), cell cycle signaling inhibitors (CDK2, CDK4, and CDK6 inhibitors) and any other cytotoxic agents, (e.g., estramustine phosphate, prednimustine).

For example, signal transduction inhibitors include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes. Growth factor receptor tyrosine kinases include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Tyrosine kinases, which are not growth factor receptor kinases are termed non-receptor tyrosine kinases. Non-receptor tyrosine kinases include cSrc, Lck, Fyn, Yes, Jak, cAbl, FAK (Focal adhesion kinase), Brutons tyrosine kinase, and Bcr-Abl.

Inhibitors of Serine/Threonine Kinases include MAP kinase cascade blockers which include blockers of Raf kinases (rafk), Mitogen or Extracellular Regulated Kinase (MEKs), and Extracellular Regulated Kinases (ERKs); and the Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases.

Inhibitors of Phosphotidyl inositol-3 Kinase family members including blockers of PI3-kinase, ATM, DNA-PK, and Ku.

Inhibitors of Ras Oncogene include inhibitors of farnesyltransferase, geranyl-geranyl transferase, and CAAX proteases as well as anti-sense oligonucleotides, ribozymes and immunotherapy.

Alkylating agents alkylate molecules such as proteins, RNA and DNA and can covalently bind these molecules.

Alkylating agents affect any point in the cell cycle and thus are known as cell cycle-independent drugs.

Antimetabolites impede DNA and RNA synthesis.

Anti-microtubule agents block cell division by preventing microtubule function.

The method can include administering the further treatment to the subject.

In an aspect, a computer-implemented method (e.g., by the processor 656 executing software 656 of computer system 602), includes calculating, by the processor, based on sequence data for a tumor 702 from a subject at a plurality of time points (e.g., 409-400 in FIG. 4), a mutation frequency for each of a plurality of SSVs at each of the time points to provide a plurality of time-resolved mutation frequencies for each of the plurality of SSVs, wherein the mutation frequency is between 0 and 1, wherein the sequence data includes the plurality of simple somatic variations (SSVs) at each of the time points, wherein N is the number of SSVs and K is the number of time points; binning, by the processor, the plurality of time-resolved mutation frequencies for each SSV to provide an N×K matrix 1002; removing matrix rows, by the processor, wherein the time-resolved mutation frequencies are less than a threshold value, and merging similar rows, to provide an N'×K matrix, wherein N'≤N; converting, by the processor, the N'×K matrix cells to pseudo-clones (e.g., 401-408), wherein each pseudo-clone represents a collection of cells defined by a set of SSVs having a defined time-resolved mutation frequency 1003; and constructing, by the processor, a time-series tumor evolution tree (e.g., 400) from the pseudo-clones (e.g., 401-408), wherein each time point in the time-series evolution tree represents an event in the subject's cancer treatment (e.g., 409-411) 1004.

In an aspect, in the method, the mutation frequency is the cancer cell fraction (CCF) or the variant allele frequency (VAF). In another aspect, the each SSV is assumed to belong to exactly one pseudo-clone. In yet another aspect, it is assumed that each SSV cannot return to its unmutated state.

In yet another aspect, each pseudo-clone has additional SSVs to the identified SSVs for the pseudo-clone.

In a still further aspect, the Goodness of Variance Fit is used during binning by the processor to determine a number of bins.

In another aspect, wherein if there is a mathematical possibility of two sub-clones being siblings, then the time-series evolution tree reflect that the two sub-clones are siblings.

Constructing, by the processor, the time-series tumor evolution tree can include placing pseudo-clones in the time-series tumor evolution tree in the least disjoint manner, according to frequency, with the most frequent pseudo-clones closer to the root of the tree. The method can further comprise determining if branching of pseudo-clones has occurred. Additionally, when new pseudo-clones appear at later time-points, the method can further comprise representing a new pseudo-clone population in the tree emerging from the root clone, or binning the new pseudo-clone within an existing pseudo-clone and adding the new pseudo-clone as an expansion of the existing pseudo-clone. Also, if a pseudo-clone frequency moves to zero, then that is viewed as a death and the pseudo-clone is terminated in the tree.

The methods can further include, determining, by the processor, an output for the subject. Exemplary outputs include that the subject is responding or not responding to a treatment based on the time-series tumor evolution tree, determining a further clinical treatment for the subject based on the time-series tumor evolution tree, or determining a time to obtain additional sequence data based on the time-series tumor evolution tree. Optionally, the further treatment is administered to the subject.

From trees developed across many subjects, patterns as to what sequence of clonal population growth and death are associated to given treatments can be identified. From these patterns, the computer can determine to start, stop or change treatments to obtain the best result for the subject. A physician can administer the treatment determined by the computer. For example, it may be determined that often in response to eribulin, a particular pseudo-clone develops, but only when that pseudo-clone reaches a frequency≥0.4 the pseudo-clone becomes resistant. The computer may determine to shift treatment to another therapy while the frequency is <0.4 to avoid that severely resistant state. This type of insight can only be made with the inventive evolutionary tree that can be strictly tied back to sample time where we can map the patient's clinical history to clonal evolution. So in that regard, this invention is important to determine outcomes for subjects based on their time-resolved tumor evolution trees.

A computer program product for cancer treatment includes a computer readable storage medium having program instructions embodied therewith, the program instructions executable by a processor to cause the processor to perform operations including: calculating, by the processor, based on sequence data for a tumor from a subject at a plurality of time points, a mutation frequency for each of a plurality of SSVs at each of the time points to provide a plurality of time-resolved mutation frequencies for each of the plurality of SSVs, wherein the mutation frequency is between 0 and 1, wherein the sequence data includes a plurality of simple somatic variations (SSVs) at each of the time points, wherein N is the number of SSVs and K is the number of time points; binning, by the processor, the plurality of time-resolved mutation frequencies for each SSV to provide an N×K matrix; removing matrix rows, by the processor, wherein the time-resolved mutation frequencies are less than a threshold value, and merging similar rows, to provide an N'×K matrix, wherein N'≤N; converting, by the processor, the N'×K matrix cells to pseudo-clones, wherein each pseudo-clone represents a collection of matrix cells defined by a set of SSVs having a defined time-resolved mutation frequency; and constructing, by the processor, a time-series tumor evolution tree from the pseudo-clones, wherein each time point in the time-series evolution tree represents an event in the subject's cancer treatment.

A system for cancer treatment includes: a processor; and a computer readable storage medium storing executable instructions that, when executed by the processor, cause the processor to perform operations including: calculating, by the processor, based on sequence data for a tumor from a subject at a plurality of time points, a mutation frequency for each of a plurality of SSVs at each of the time points to provide a plurality of time-resolved mutation frequencies for each of the plurality of SSVs, wherein the mutation frequency is between 0 and 1, wherein the sequence data includes a plurality of simple somatic variations (SSVs) at each of the time points, wherein N is the number of SSVs and K is the number of time points; binning, by the processor, the plurality of time-resolved mutation frequencies for each SSV to provide an N×K matrix; removing matrix rows, by the processor, wherein the time-resolved mutation frequencies are less than a threshold value, and merging similar rows, to provide an N'×K matrix, wherein N'≤N; converting, by the processor, the N'×K matrix cells to pseudo-clones, wherein each pseudo-clone represents a collection of matrix cells defined by a set of SSVs having a defined time-resolved mutation frequency; and constructing, by the processor, a time-series tumor evolution tree from the pseudo-clones, wherein each time point in the time-series evolution tree represents an event in the subject's cancer treatment.

FIG. 6 depicts a system 600 according to embodiments of the invention. Network 601 and computer system 602 can be used to store and communicate sequence data for tumors from one or more subjects, to calculate a matrix of SSVs and frequencies, and to calculate time-series tumor evolution tree. Also using the computer-implemented process, the time series evolution tree (e.g., 400 in FIG. 4) is used to make a treatment decision 606 which can then be administered to a patient. The computer system 602 includes one or more processors 650, memory 652, and one or more software applications 656 having computer-executable instructions to function as discussed herein. The processors 650 are configured to the execute computer-executable instructions of the software applications 656.

FIG. 7 illustrates aspects of the computer-implemented method 700 executed by the software application 656. Tumor sequence data 702 is obtained including a plurality of SSVs and their frequencies at a plurality of time-points in a subject's cancer treatment. The SSVs are binned according to their frequencies, e.g., by processor 605 and software applications 656 depicted in FIG. 6, to provide a matrix 704 of SSVs and their frequencies at each of the plurality of time-points. The matrix 704 is then used to construct a time-series phylogenetic tree 705 e.g., by processor 605 and software applications 656 depicted in FIG. 6, for the subject.

Figure 10:
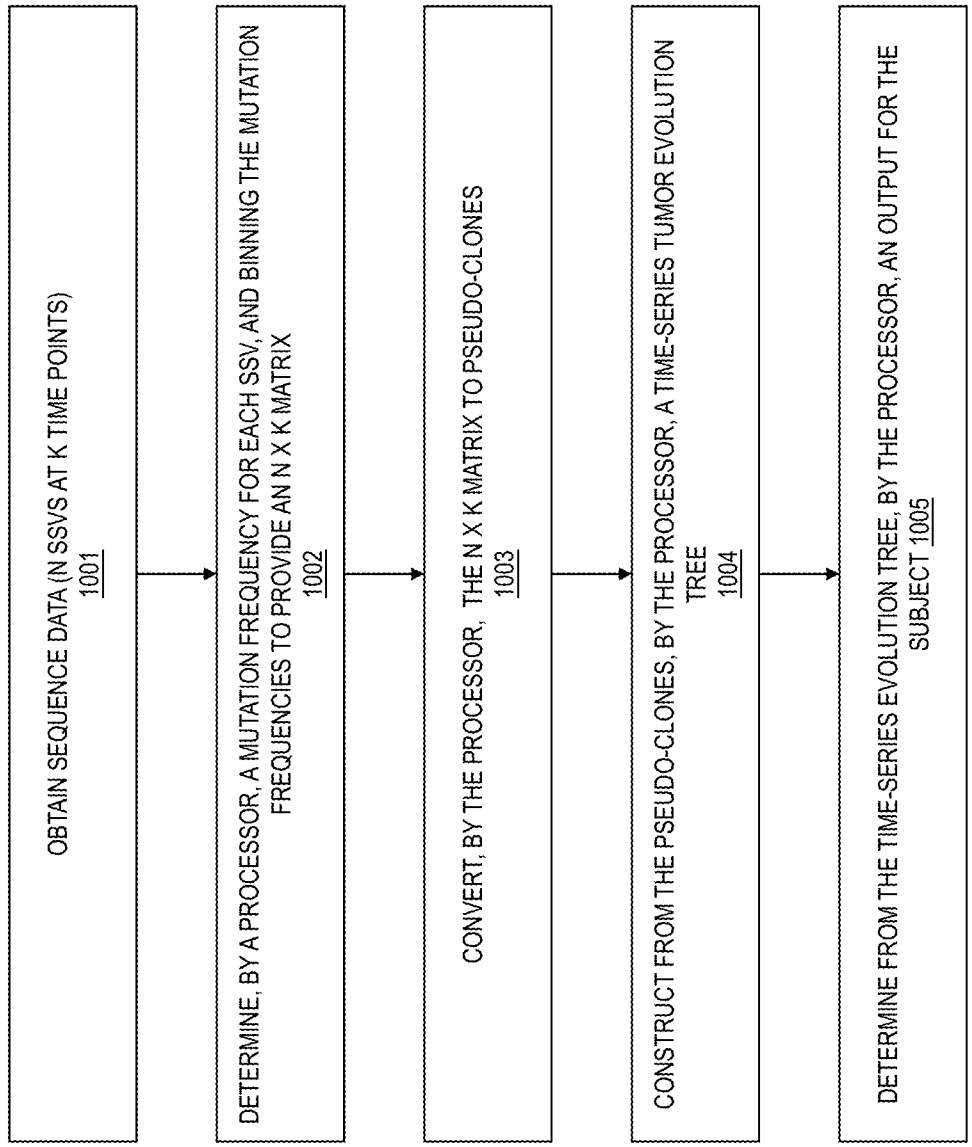
FIG. 10 is a flowchart of a computer-implemented method for constructing a time-series tumor evolution tree according to embodiments of the present invention.

FIG. 10 is a flowchart of a computer-implemented method 1000 by computer system 602 for constructing time-series tumor evolution trees according to embodiments of the present invention. At block 1001, sequence data including N SSVs at K time points is obtained by the computer system 602. At block 1002, a mutation frequency is determined for each SSV (by the computer system 602) and the mutation frequencies are binned (by the computer system 602) to provide an N×K matrix. At block 1003, the N×K matrix is converted to pseudo-clones by the computer system 602. At block 1004, a time-series evolution tree is constructed from the pseudo-clones by the computer system 602). And at block 1005, an output for the subject is determined from the time-series evolution tree by the computer system 602.

Figure 11:
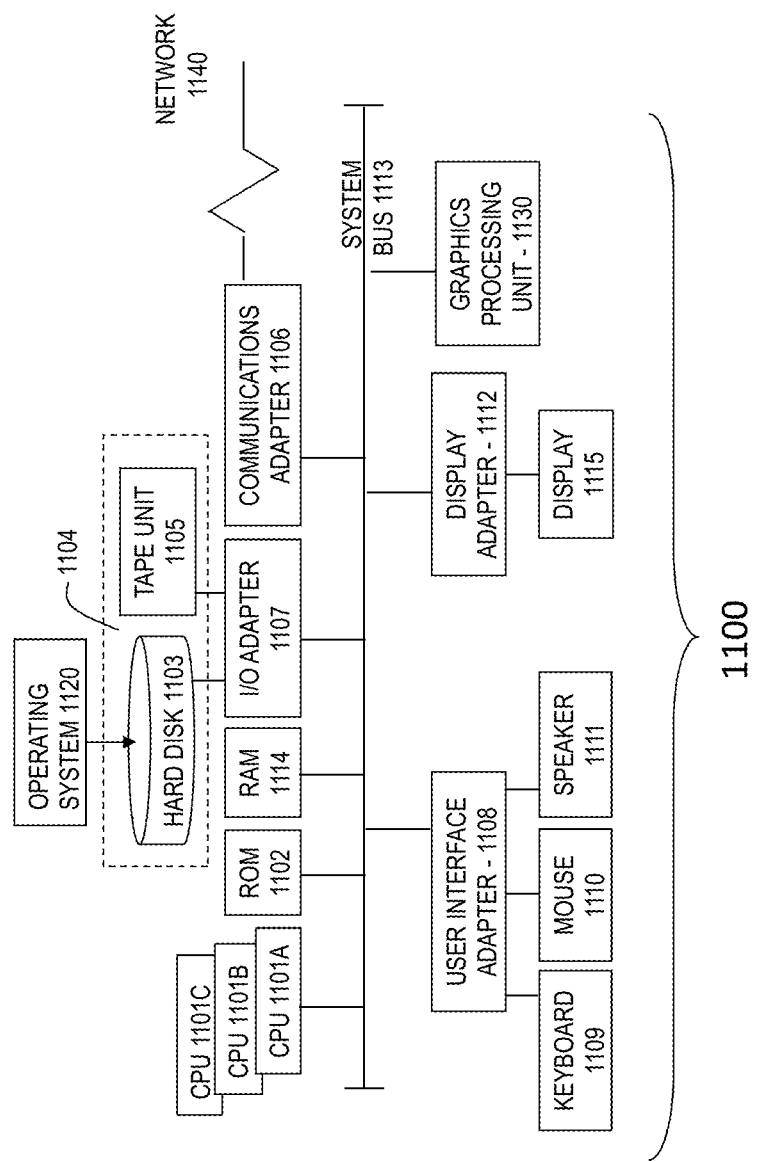
FIG. 11 depicts a computer/processing system having components and/or functionality for practicing one or more embodiments of the present invention.

FIG. 11 depicts exemplary components of a computer system 1100 according to one or more embodiments of the present invention. Any of the elements and functionality of computer system 1100 can be included in any of the elements in FIGS. 1-10. Particularly, computer system 602 can implement the elements of computer system 1100 to perform the functions discussed herein. The computer system 600 is a processing system. The processing system 1100 can include one or more central processing units (processors) 1101A, 1101B, 1101C, etc. (collectively or generically referred to as processor(s) 1101). In one or more embodiments, each processor 1101 can include a reduced instruction set computer (RISC) microprocessor. Processors 1101 are coupled to system memory 1114 and various other components via a system bus 1113. Read only memory (ROM) 1102 is coupled to the system bus 1113 and can include a basic input/output system (BIOS), which controls certain basic functions of processing system 600.

FIG. 11 further depicts an input/output (I/O) adapter 1107 and a network adapter 1106 coupled to the system bus 1113. I/O adapter 1107 can be a small computer system interface (SCSI) adapter that communicates with a hard disk 1103 and/or tape storage drive 1105 or any other similar component. I/O adapter 1107, hard disk 1103, and tape storage device 1105 are collectively referred to herein as mass storage 1104. Operating system 1120 for execution on the processing system 1100 can be stored in mass storage 1104. The network adapter 1106 interconnects bus 1113 with an outside network, for example, network 1140, enabling data processing system 1100 to communicate with other such systems. A screen (e.g., a display monitor) 1115 is connected to system bus 1113 by display adaptor 1112, which can include a graphics adapter to improve the performance of graphics intensive applications and a video controller. In one or more embodiments of the present invention, adapters 1107, 1106, and 1112 can be connected to one or more I/O busses that are connected to system bus 613 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 1113 via user interface adapter 1108 and display adapter 1112. A keyboard 1109, mouse 1110, and speaker 1111 all interconnected to bus 1113 via user interface adapter 1108, which can include, for example, a Super I/O chip integrating multiple device adapters into a single integrated circuit.

In exemplary embodiments, the processing system 1100 includes a graphics processing unit 1130. Graphics processing unit 1130 is a specialized electronic circuit designed to manipulate and alter memory to accelerate the creation of images in a frame buffer intended for output to a display. In general, graphics processing unit 1130 is very efficient at manipulating computer graphics and image processing and has a highly parallel structure that makes it more effective than general-purpose CPUs for algorithms where processing of large blocks of data is done in parallel.

Thus, as configured in FIG. 11, the processing system 1100 includes processing capability in the form of processors 1101, storage capability including system memory 1114 and mass storage 1104, input means such as keyboard 1109 and mouse 1110, and output capability including speaker 1111 and display 1115. In one implementation, a portion of system memory 1114 and mass storage 1104 collectively store an operating system coordinate the functions of the various components shown in FIG. 11.

The present invention can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user' s computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising
calculating, by a processor, based on sequence data for a tumor from a subject at a plurality of time points, a mutation frequency for each of a plurality of simple somatic variations (SSVs) at each of the time points to provide a plurality of time-resolved mutation frequencies for each of the plurality of SSVs, wherein the mutation frequency is between 0 and 1, wherein the sequence data comprises the plurality of SSVs at each of the time points, wherein N is the number of SSVs and K is the number of time points;
binning, by the processor, the plurality of time-resolved mutation frequencies for each SSV at each of the time points to provide an N×K matrix;
removing matrix rows, by the processor, wherein the time-resolved mutation frequencies are less than a threshold value, and merging similar rows, to provide an N'×K matrix, wherein N'≤N;
converting, by the processor, the N'×K matrix cells to pseudo-clones, wherein each pseudo-clone represents a collection of matrix cells defined by a set of SSVs having a defined time-resolved mutation frequency, wherein each SSV is assumed to belong to exactly one pseudo-clone, and wherein it is assumed that each SSV cannot return to its unmutated state;
constructing, by the processor, a time-series tumor evolution tree from the pseudo-clones, wherein each time point in the time-series evolution tree represents an event in the subject's cancer treatment and is associated with the defined time-resolved mutation frequency;
determining that a new cancer treatment for the subject, different from the subject's cancer treatment previously used, is needed to avoid a resistant state based at least in part on a value of the defined time-resolved mutation frequency, wherein a shift to the new cancer treatment is to maintain the value of the defined time-resolved mutation frequency below a predetermined mutation frequency value; and
responsive to determining that the new cancer treatment is needed for the subject to maintain the value of the defined time-resolved mutation frequency below the predetermined mutation frequency value thereby avoiding the resistant state, administering the new cancer treatment to the subject, the new cancer treatment, different from the subject's cancer treatment previously used, comprises a selection of a signal transduction pathway inhibitor, an antimetabolite, an antimicrotubule agent, an alkylating agent, a nitrogen mustard, a nitrosourea, a platinum agent, an anthracycline, an antibiotic, a topoisomerase inhibitor, an alkyl sulfonate, a triazine, an ethyenimine, a folic acid analog, a pyrimidine analogue, a purine analog, an antitumor antibiotic, a hormone, an anti-angiogenic agent, an immunotherapeutic agent, a cell cycle signaling inhibitor, or a combination thereof, wherein stopping the subject's cancer treatment previously used is to avoid the resistant state.

2. The computer-implemented method of claim 1, wherein the mutation frequency is the cancer cell fraction (CCF) or the variant allele frequency (VAF).

3. The computer-implemented method of claim 1, wherein each pseudo-clone has additional SSVs to the identified SSVs for the pseudo-clone.

4. The computer-implemented method of claim 1, wherein the Goodness of Variance Fit is used during binning by the processor to determine a number of bins.

5. The computer-implemented method of claim 1, wherein if there is a mathematical possibility of two sub-clones being siblings, then the time-series evolution tree reflect that the two sub-clones are siblings.

6. The computer-implemented method of claim 1, wherein the subject's cancer treatment comprises radiation therapy, surgery, chemotherapy, targeted therapy, hormone therapy, immunotherapy, stem cell transplant, or a combination comprising at least one of the foregoing.

7. The computer-implemented method of claim 1, further comprising determining an outcome for the subject.

8. The computer-implemented method of claim 7, wherein the outcome comprises determining, by the processor, that the subject is responding or not responding to a treatment based on the time-series tumor evolution tree, determining a further clinical treatment for the subject based on the time-series tumor evolution tree, or determining a time to obtain additional sequence data based on the time-series tumor evolution tree.

9. The computer-implemented method of claim 1, further comprising determining a growth or a shrinkage of the pseudo-clones over time in response to the subject's cancer treatment; and determining a timing for a next assay for the subject according to the growth or the shrinkage of the pseudo-clones.

\* \* \* \* \*